United States Patent [19]

Enloe

[11] Patent Number: 4,761,258
[45] Date of Patent: Aug. 2, 1988

[54] CONTROLLED FORMATION OF LIGHT AND HEAVY FLUFF ZONES

[75] Inventor: Kenneth M. Enloe, Neenah, Wis.

[73] Assignee: Kimberly-Clark Corporation, Neenah, Wis.

[21] Appl. No.: 807,380

[22] Filed: Dec. 10, 1985

[51] Int. Cl.$^4$ .................. D04H 1/04; D04H 17/00
[52] U.S. Cl. .................. 264/518; 264/118; 264/121; 425/80.1; 425/83.1
[58] Field of Search .......... 264/121, 517, 518, 118, 264/119; 425/81.1, 80.1, 82.1, 83.1; 19/148

[56] References Cited

U.S. PATENT DOCUMENTS

| | | | |
|---|---|---|---|
| 3,501,813 | 3/1970 | Lee et al. | 19/156.3 |
| 3,518,726 | 7/1970 | Banks | 19/144.5 |
| 3,598,680 | 8/1971 | Lee | 156/377 |
| 3,682,761 | 8/1972 | Lee et al. | 161/124 |
| 3,757,785 | 9/1973 | Wosaba, II | 128/287 |
| 3,766,922 | 10/1973 | Krusko | 128/284 |
| 3,848,598 | 11/1974 | Mesek | 128/287 |
| 3,860,002 | 1/1975 | Kolbach | 128/284 |
| 3,924,626 | 12/1975 | Lee et al. | 128/287 |
| 3,939,240 | 2/1976 | Savich | 264/91 |
| 3,962,753 | 6/1976 | Dunn | 19/156.3 |
| 3,973,291 | 8/1976 | Kolbach | 19/148 |
| 3,975,222 | 8/1976 | Mesek | 156/62.2 |
| 3,994,047 | 11/1976 | Lee et al. | 19/156.3 |
| 4,005,957 | 2/1977 | Savich | 425/80 |
| 4,016,628 | 4/1977 | Kolbach | 19/148 |
| 4,103,058 | 6/1978 | Humlicek | 428/171 |
| 4,223,677 | 9/1980 | Anderson | 128/287 |
| 4,388,056 | 6/1983 | Lee et al. | 425/83.1 |
| 4,592,708 | 6/1986 | Feist et al. | 425/80.1 |

Primary Examiner—Jan H. Silbaugh
Assistant Examiner—Mary Lynn Fertig
Attorney, Agent, or Firm—Paul Yee

[57] ABSTRACT

The present invention provides an improved apparatus for forming a fibrous web, and includes a fibrous supply mechanism for providing fibers of web material. The fibers are deposited onto a foraminous web forming layer which may optionally have a pocket recess formed therein. A foraminous spacing mechanism supports the web forming layer while allowing a substantially unrestricted gas flow from a region immediately adjacent to and downstream from the web forming layer. A gas flow regulating layer has a selected pattern of apertures therethrough, and is fixedly positioned in adjacent facing relation with the foraminous spacing means. The regulating layer provides a selected pattern of gas flow through the web forming layer. The regulating layer, the foraminous spacing mechanism and the gas flow regulating layer are constructed to form an installable and replaceable assembly, and a flow forcing mechanism provides a flow of gas through the web forming layer.

28 Claims, 9 Drawing Sheets

CONTROLLED FORMATION OF LIGHT AND HEAVY FLUFF ZONES

FIELD OF THE INVENTION

The present invention relates to a method and apparatus for forming air-laid fibrous webs. More particularly, the invention relates to a method and apparatus for forming an absorbent batt that has tailored absorbency zones. Certain zones or areas have a higher basis weight and a correspondingly higher absorbency than other zones.

BACKGROUND OF THE INVENTION

Absorbent disposable articles, such as diapers, feminine napkins and incontinence garments, employ absorbent batts to absorb body fluids, such as urine. It has generally been desirable to form a contoured batt or pad which locates more absorbent material in those areas which are subjected to higher levels of fluid loading. Various types of conventional machines have been employed to manufacture such contoured pads.

U.S. Pat. No. 4,388,056 issued June 14, 1983 to F. B. Lee, et al. discloses an apparatus for continuously forming a cyclically contoured and densified air-laid fibrous web. The web has alternately spaced narrow regions with relatively high basis weight and wide regions with relatively low basis weight. Adjustable shutter plates are configured to span a plurality of transverse plenum segments to modulate the air flow through the device.

U.S. Pat. No. 3,682,761 issued Aug. 8, 1972 to C. A. Lee, et al. discloses a device for forming an elongated air-laid web. This web has a longitudinally extending central portion and integral longitudinally extending portions flanking the central portion. This web also has a generally stepped configuration with a greater average thickness in the central portion than in the side portions. The device taught by C. A. Lee, et al. employs baffles to direct more fibrous material toward the central portion of the web, and employs a plurality of valves to increase the amount of suction through the central portion of the web to induce the formation of a greater thickness at that central portion.

U.S. Pat. No. 4,005,957 issued Feb. 1, 1977 to P. Savich discloses a device which has a screen with pockets formed therein and which is employed to manufacture fibrous pads.

U.S. Pat. No. 3,973,291 issued Aug. 10, 1976 to C. G. Kolbach discloses a method and apparatus for forming discrete fibrous pads which have contoured thickness. The method and apparatus disclosed by Kolbach employ a sequence of masks which completely block off a source of applied vacuum to all sections of each pad receiving compartment except that section in which a region of a fibrous pad having a particular weight of fibers per unit area is to be formed.

U.S. Pat. No. 4,016,628 issued Apr. 12, 1977 to C. C. Kolbach discloses a device for forming an air-laid fibrous web having a medial portion of greater basis weight than flanking end and side portions. The apparatus includes a vacuum box which has an open end underlying a discrete section of a foraminous forming surface. Vacuum connection means establish a greater pressure drop across the discrete section of the foraminous forming surface overlying the open end of the vacuum box than across the regions of the foraminous forming surface extending beyond the edges of the vacuum box.

U.S. Pat. No. 3,962,753 issued June 15, 1976 to J. W. Dunn discloses a device for forming a fibrous glass strand mat. The apparatus includes a panel having a plurality of spaced apertures located underneath a foraminous conveyor. The plate creates a back pressure and a relatively static high pressure area immediately above the conveyor. This eliminates the problem of random movement of the fibers after deposition on the conveyor, and reduces the air circulation to permit an even distribution of the fibers on the mat.

U.S. Pat. No. 4,103,058 issued July 25, 1978 to L. D. Humlicek discloses a blown microfiber web having a network of compacted high-density regions and pillowed low density regions. The web may be collected on a perforated screen so that the microfibers deposited on the land area of the screen form the compacted high density regions and microfibers deposited over the openings of the screen formed the pillowed low density regions.

Conventional devices, such as those taught by the above references, have been difficult to adjust. In particular, these devices have required complicated adjustments to moveable plate elements located inside the forming mechanism, or have required complicated arrangements of compartments and multiple vacuum suction means for providing different amounts of applied suction to selected regions of a forming screen.

SUMMARY OF THE INVENTION

The present invention provides a distinctive method and apparatus for forming a fibrous web. Generally stated, the apparatus includes a fiber supply means for providing fibers of web material. These fibers are deposited on a foraminous web forming layer, which is supported by a foraminous spacing means. The foraminous spacing means supports the web forming layer in a configuration which allows a substantially unrestricted gas flow from a region immediately adjacent to and downstream from the web forming layer. A gas flow regulating layer has a selected pattern of apertures therethrough, and is fixedly positioned in adjacent, facing relation with the foraminous spacing means to provide a selected pattern of gas flow through the web forming layer. The foraminous web forming layer, the foraminous spacing means and the gas flow regulating layer are constructed to form an installable and replaceable assembly, and flow forcing means provide a selected flow of gas through the web forming layer.

The invention further provides a method for forming a fibrous web, which includes the step of depositing fibers of web material onto a foraminous web forming layer. The web forming layer is supported in a configuration which allows a substantially unrestricted gas flow from a region immediately adjacent to and downstream from the web forming layer. A selected pattern of gas flow is directed through the web forming layer by a gas flow regulating layer, which has a selected pattern of apertures therethrough and is fixedly positioned downstream from the web forming layer. The foraminous web forming layer, the foraminous spacing means and the gas flow regulating layer are constructed to form an installable and replaceable assembly, and a suitable flow of gas is forced through the web forming layer.

The method and apparatus of the invention can advantageously provide a web forming assembly which includes a gas flow regulating mechanism and is readily installable on and removable from an outside portion of a transport means. The regulating mechanism is readily adjusted to produce a desired distribution of fiber basis weight across the formed web. Maintenance and set-up time can be reduced, and the forming assembly is less susceptible to clogging by the fibers.

BRIEF DESCRIPTION OF THE DRAWINGS

The invention will be more fully understood and further advantages will become apparent when reference is made to the following detailed description of the invention and the following drawings in which.

DETAILED DESCRIPTION OF THE INVENTION

The method and apparatus of the present invention are particularly useful for forming contoured fibrous webs or pads which have an increased weight of material in selected regions. When forming pads of absorbent material, the regions with greater weight of material generally have a corresponding greater degree of absorbency. Such contoured absorbent pads are particularly useful in articles that are subjected to a greater fluid loading in certain "target" areas than in other areas. For example, in a baby diaper comprised of the absorbent batt or pad is located between a liquid pervious inner layer and a liquid impervious outer layer, the crotch and front areas of the diaper are more heavily wetted by the infant than the areas closer to the infant's waist or back. A similar situation may also arise in the case of wound dressings, incontinence garments and feminine sanitary napkins.

While the following detailed description will be made in the context of the manufacture of a disposable diaper, it will be readily apparent that the method and apparatus of the present invention can be employed to produce fibrous webs or pads for other types of articles which require a greater weight of material in selected regions. Such articles would include, for example, incontinence garments, sanitary napkins and the like, all of which are contemplated as being within the scope of the invention.

In the following description, the term "basis weight" is intended to designate the weight of fiber material per unit surface area of the web. For example, typical units would be grams/cm$^2$.

The material employed to form the fibrous web is typically composed of an absorbent material, such as a cellulosic material commonly known as "fluff", or the like. In addition, the web material may include a coformed mixture of cellulosic fibers with polymeric fibers, such as polypropylene fibers, polyethylene fibers, or the like. The precursor web material is generally supplied in sheet form, wound into a roll.

Figure 1:
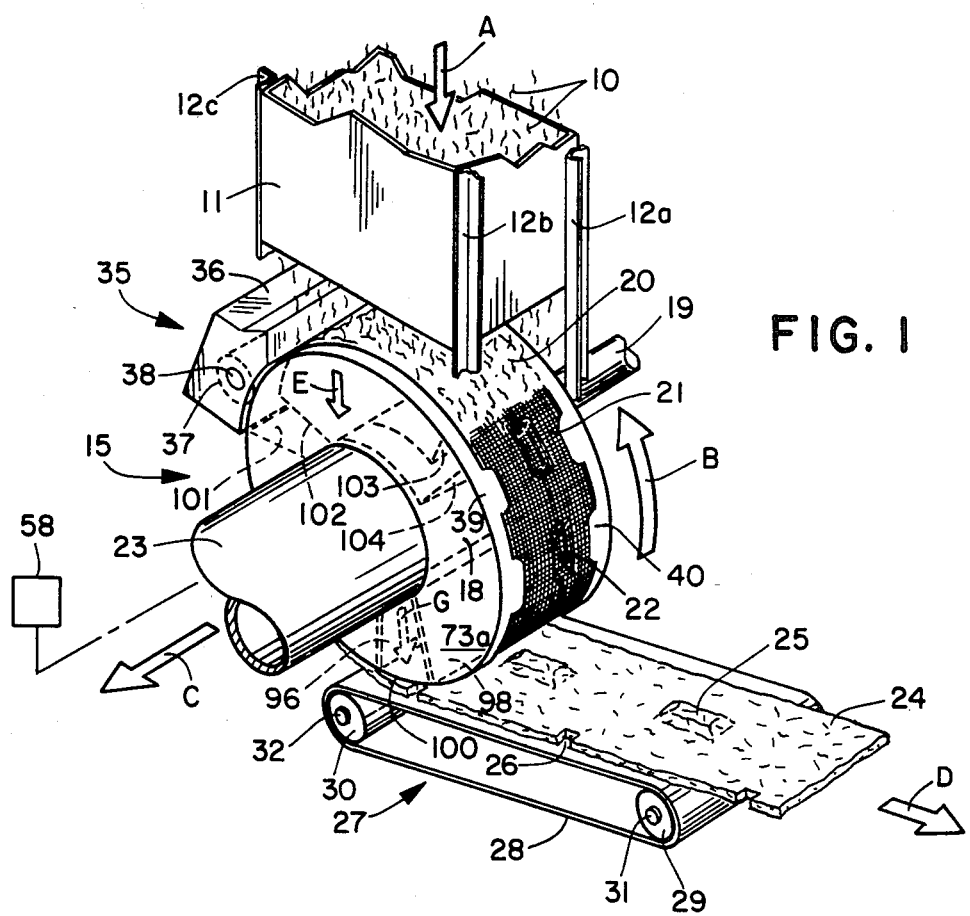
FIG. 1 representatively shows a perspective view of a forming drum which can be employed with the method and apparatus of the invention.

Referring now to the drawings, FIG. 1 shows a representative apparatus suitable for forming a laid fibrous article in accordance with the present invention. Fibers 10, which enter the system as air-entrained fibers in a stream flowing in the direction indicated by Arrow A, may suitably be derived from a supply of cellulosic, e.g., wood pulp, fibers or other natural or synthetic fibers, which have been subjected to fiberization treatment, i.e., picked apart, in a manner known in the art to provide loose fibers. The fibers may be entrained in any other suitable gaseous medium, and references to "air" as the entraining medium herein will be understood to encompass all such other entrainment fluids.

The stream of air-entrained fibers passes by means of flow channel housing 11 to the forming drum assembly 15. The flow channel housing serves to direct and concentrate the air-entrained fibers and to provide a uniform velocity profile in the air/fibers stream. The flow channel housing is supported by support members 12a-c, which aggregately form a support frame for the housing and may be anchored and/or joined to other suitable structural elements as necessary or desirable. The fibers deposit onto an upstream surface of a replaceable, foraminous web forming assembly 21, which is located on an outer peripheral rim section of a substantially cylindrical drum 18.

In the present description, the terms "downstream" and "upstream" are determined with respect to the direction of gas flow produced by gas flow forcing means 58. In the shown embodiments, this gas flow direction is generally from top to bottom and from the outside of drum 18 to the inside of the drum. With respect to a particular reference point or location, "upstream" refers to an orientation in which the gas stream is approaching the reference location, and "downstream" refers to an orientation in which the gas stream is departing from the reference location. Thus, for example, the upstream surface of web forming assembly 15 is an outwardly facing surface, and the downstream surface of the assembly is an inwardly facing surface.

Figure 4:
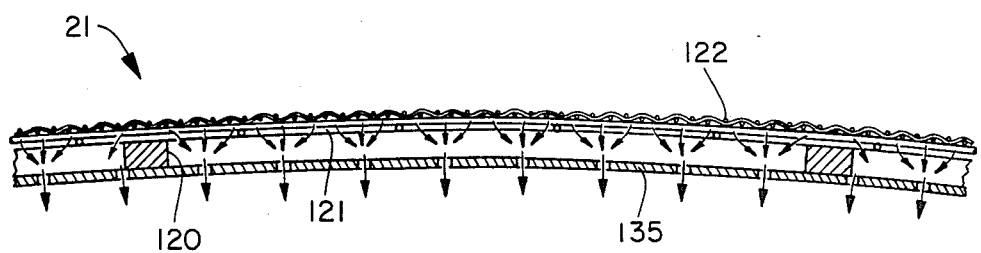
FIG. 4 representatively shows a detailed, cross-sectional view of the multi-layer forming assembly of the forming drum.
Figure 5:
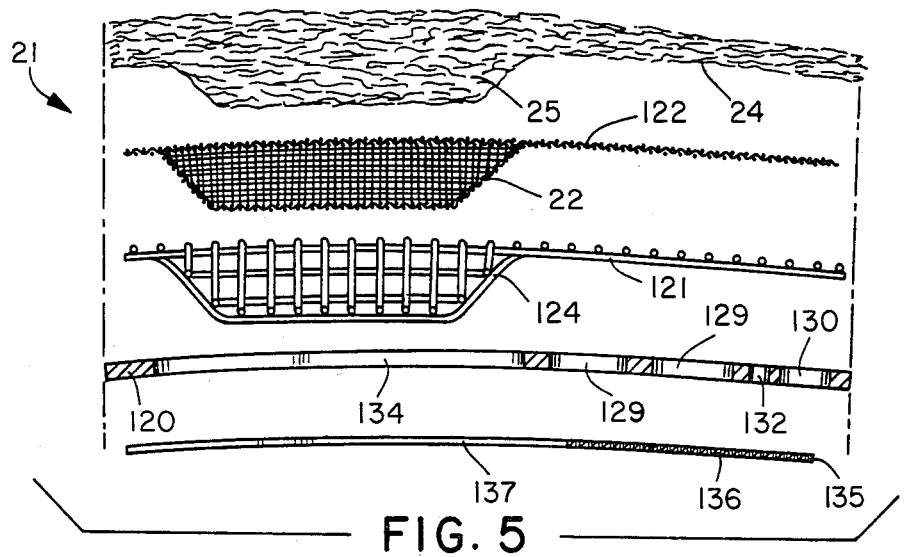
FIG. 5 representatively shows an exploded, cross-sectional view of another embodiment of the multi-layer forming assembly, which includes a pocket recess.

As representatively shown in FIGS. 4 and 5, web forming assembly 21 includes a foraminous web forming layer 122, which has an optional pocket recess 22 formed therein and which receives a deposit of the fibers of web material thereon. A foraminous spacing means, such as one comprised of hardware cloth 121 and spacer sheet member 120, supports web forming layer 122 while allowing a substantially unrestricted gas flow from a region immediately adjacent to and downstream from the web forming layer. A gas flow regulating layer 135 has a selected pattern of apertures therethrough and is fixedly positioned in adjacent, facing relation with the foraminous spacing means. This flow regulating layer provides a selected pattern of gas flow through web forming layer 122. The combination of the web forming assembly, the foraminous spacing means and the gas flow regulating layer provides a web forming assembly, which as a unit can be replaceably mounted on a selected transport means.

Referring again to FIG. 1, a transport means, such as rotatable drum assembly 15, moves multi-layer web forming assembly 21 along a path which traverses through fiber forming chamber 11. Alternatively, the transport means may be comprised of a moveable, endless belt or conveyor, such as representatively shown in U.S. Pat. No. 3,973,291.

Gas flow forcing means 58, such as a suction pump fan, draws air out from suction chambers formed within drum assembly 15 by way of conduit 23. As a result, the pump fan creates a pressure differential across multi-layer web forming assembly 21 between the suction chambers and fiber forming chamber 11. This pressure differential, which can range from about 15–25 inches water (about 3.74–6.22 kPa), draws the fibers from chamber 11 onto that portion of the surface of web forming assembly 21 located within the boundary confines of the fiber forming chamber.

Figure 2:
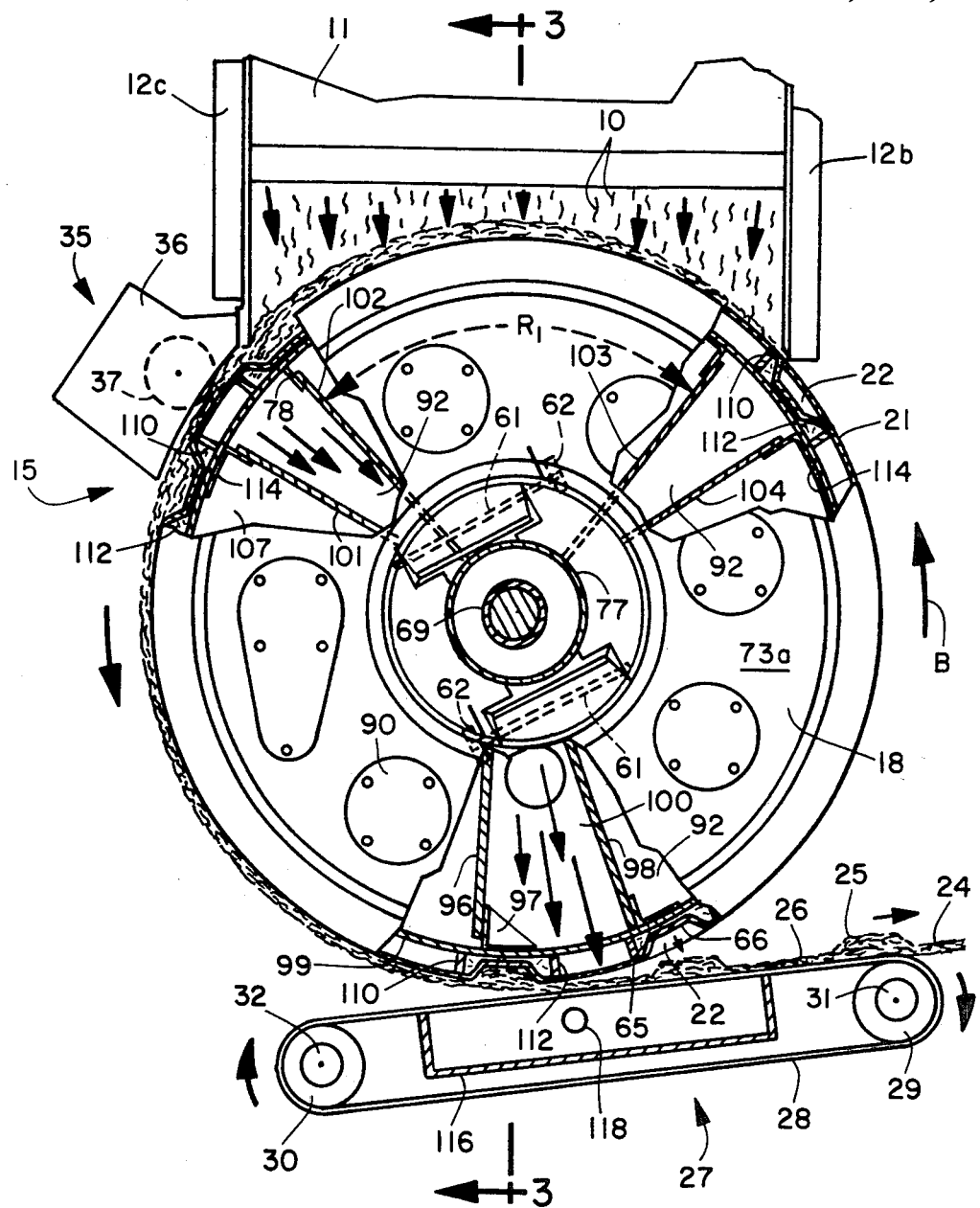
FIG. 2 representatively shows a side elevational view of the forming drum apparatus.
Figure 3:
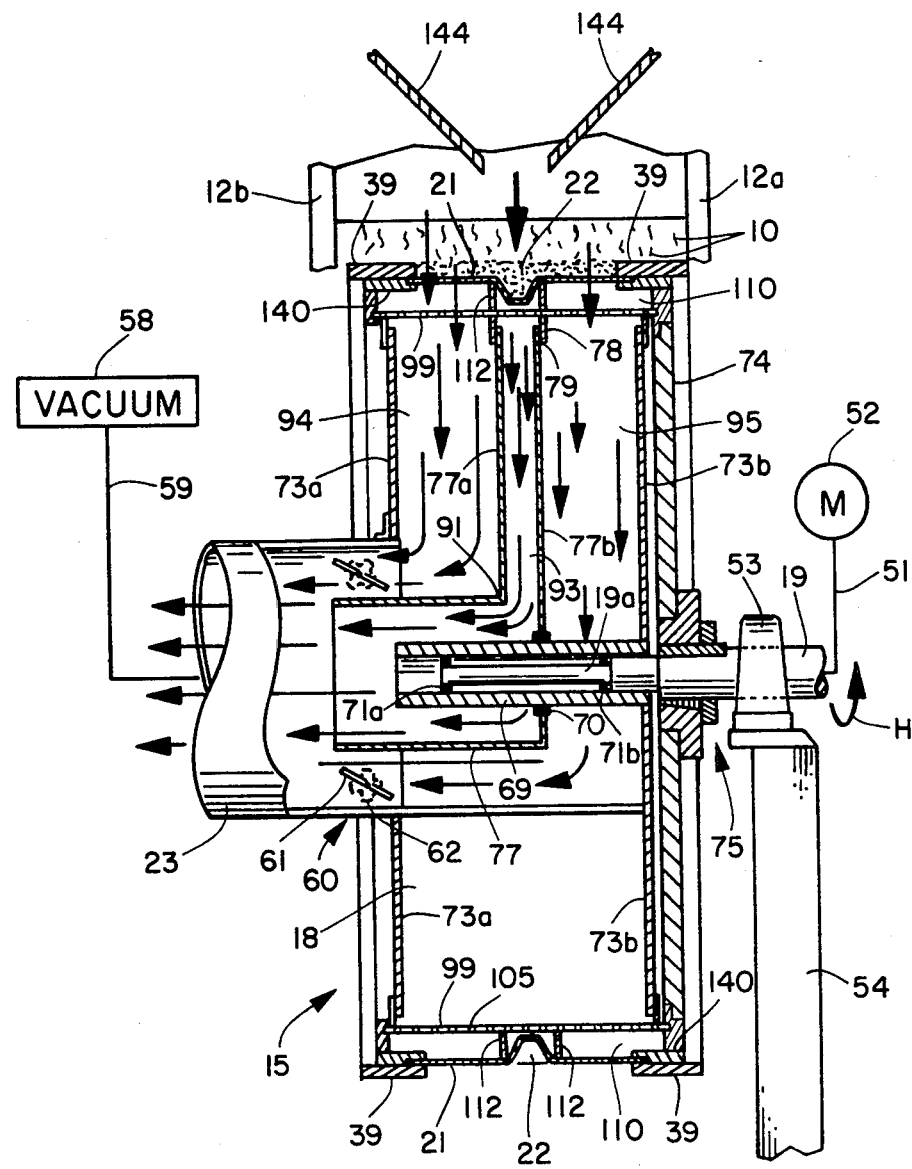
FIG. 3 representatively shows a cross-sectional, end view of the forming drum.

As representatively shown in FIGS. 2 and 3, drum assembly 15 rotates about shaft 19 to carry web forming assembly 21 through fiber forming chamber 11 and to carry formed web 24 out from chamber 11 to a shaping means, such as scarfing roll 37. Scarfing roll 37 rotates about a shaft and contacts the radially outwardly facing free surface of web 24. The movement of the peripheral surface of scarfing roll 37 removes uneven spots from the free surface of web 24 to produce a more uniform and level outer surface on the web. A further rotation of drum 18 carries web 24 around to conveyor means 27. This conveyor is generally comprised of a flexible screen mesh in the form of an endless belt that moves around a path defined by guide rollers. The guide rollers are driven by suitable drive means, such as an electric motor (not shown) to transport web 24 to a desired location. Web 24 generally detaches itself from web forming assembly 21 by reason of its own weight and drops onto conveyor 27. Optionally, a selected gas pressure can be applied to help remove web 24 from web forming assembly 21 and drum assembly 15.

The forming drum assembly 15 comprises a forming drum 18 which is rotatable in the direction of Arrow B. Rotation of the drum is affected by means of the forming drum drive shaft 19 which may be joined to suitable drive means (not shown) such as an electric or other motor directly or indirectly coupled to such shaft. The forming drum comprises an air-laid fibrous web laydown zone 20 positioned beneath the air/fibers flow channel housing 11 and configured as a vacuum laydown zone of the foraminous, web forming assembly 21. This vacuum laydown zone constitutes a circumferential cylindrical surface portion of the rotatable drum. The vacuum laydown surface has imposed thereon a pressure differential under the action of vacuum suction means (not shown), such as an exhaust blower or other suitable suction means, which suctioningly withdraws air from the arcuate segment of the forming drum associated with the vacuum laydown surface through the air discharge (suction) duct 23, in a manner more fully described hereinafter. The foraminous web forming assembly 21 can optionally have therein a series of circumferentially spaced-apart, inverted, generally frusto-pyramidal shaped depressions or pockets provided by contoured surface portions 22 in the surface thereof, of elongate form with their longitudinal axes coincident with the center line of the web forming assembly 21, i.e., the surface portions 22 are typically centered on the forming surface relative to the cross-machine direction.

As described more fully hereinafter, the forming drum contains a series of radially extending wall members or baffles 101, 102, 103, 104, 98 and 96, which are stationary, as described more fully in connection with FIGS. 2 and 3 herein.

Thus, under the influence of vacuum suction means, air in the air-entrained fibers stream is drawn through the web forming assembly 21 into the interior of the forming drum, between baffle plate members 102 and 104, in the directions indicated by Arrow E, subsequently passing out of the drum through the discharge duct 23 in the direction of Arrow C. As the air-entrained fibers stream impinges on the web forming assembly 21, only the air component thereof is passed through and the fibers component of the stream is retained on the forming surface to form a nonwoven fibrous web thereon. Subsequently, with rotation of the drum, the formed web 24 is removed from the forming surface under the influence of gravity by the weight of the fibrous web 24 and with a pressure differential produced, for example, by pressurized air in blow-off zone 100, between baffle plate members 98 and 96, and flowing outwardly through the forming surface in the direction shown by Arrow G. The combination of the pressure differential across the forming surface at the annular blow-off zone 100, combined with the weight of the fibrous web 24 and the conformation of the contoured surface portions (depressions) 22, as hereinafter described, results in a readily removed fibrous web.

The web 24 is removed from the forming surface onto take-off conveyor 27 comprising endless conveyor belt 28 disposed about rollers 29 and 30, which are respectively positioned on roller shaft members 31 and 32. The longitudinally extending fibrous web as removed on the take-off conveyor 27 features a pad 25 corresponding to the concavely contoured surface portions 22 on the forming surface.

Figure 8:
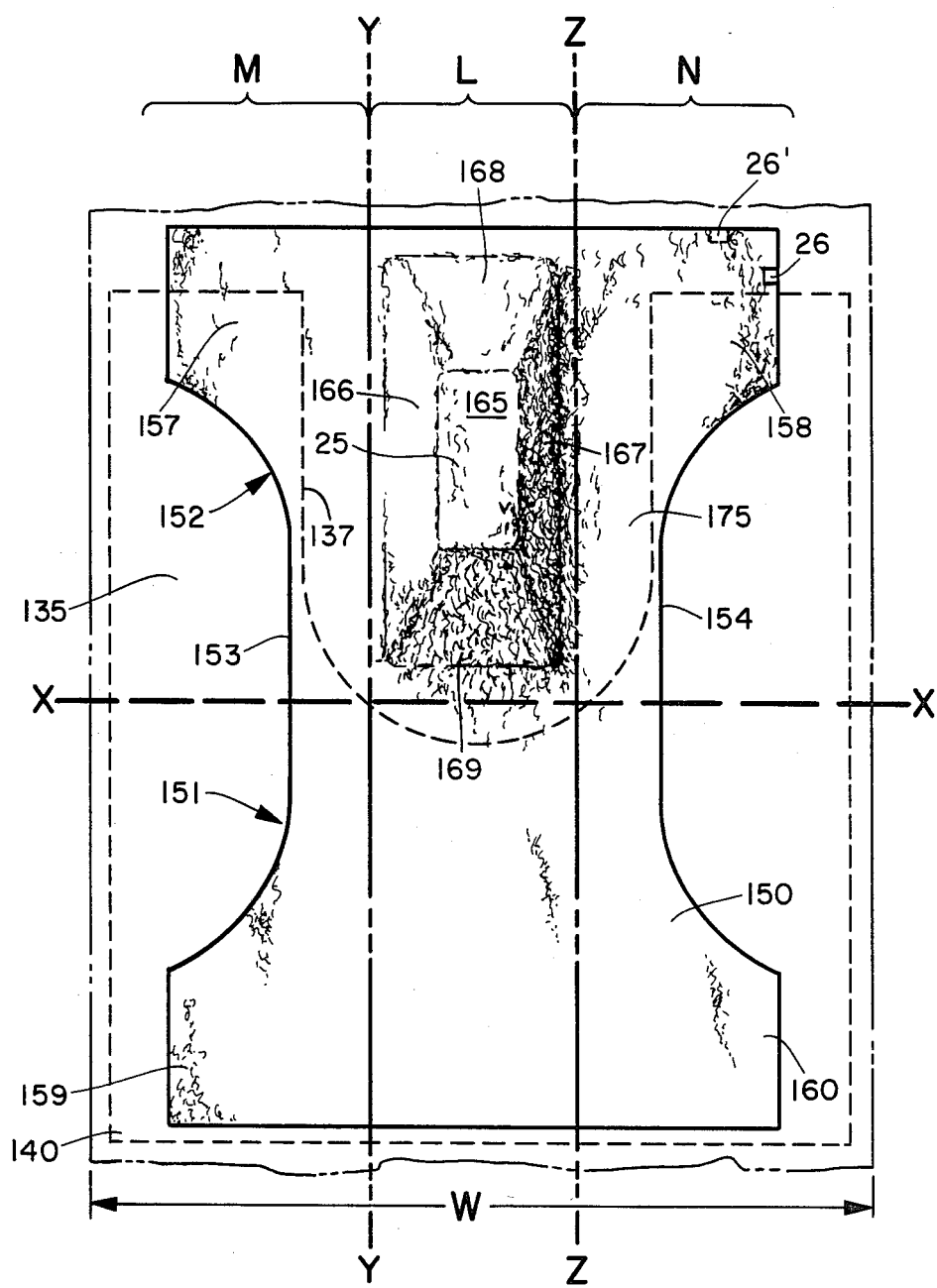
FIG. 8 shows a plan view of a representative fibrous article.

In addition to the blocking plate rings 39, the forming surface may also have disposed thereon symmetrically opposed arcuate blocking plates 40, as shown. These blocking plates are particularly advantageous when the forming drum assembly is employed to produce absorbent webs for use in disposable diapers and the like, whereby the blocking plates 40 prevent deposition of fibers on the forming surface to form corresponding arcuate cut-out sections on the finished web (not shown in FIG. 1, but as indicated in FIG. 8 by the edges 153, 154).

The longitudinally extending fibrous web 24 prior to its removal from the forming drum passes through the scarfing zone defined by the scarfing roll assembly 35. The scarfing roll assembly in turn comprises scarfing roll housing 36 containing scarfing roll 37 disposed on a scarfing roller shaft member 38, driven by means which for simplicity are not shown, but which may be any suitable motive means, and for example may involve coupling by gear or other means to the motor or drive means for the rotatable drum 18. The scarfing roll assembly constitutes trimming means for trimming the excess radial thickness of the laid fibrous web deposited on the web forming assembly 21 to yield a laid fibrous web having a substantially uniform, flat cross-direction contour on one major face surface thereof. The scarfing roll 37 is disposed in spaced adjacent relationship to the forming surface, and the scarfing roll and the forming surface are translated relative to one another in opposite directions, to remove excess thickness of the fibrous web. A transporting means, such as a suction fan, (not shown) draws the removed fibrous material away from the formed fibrous web and out from scarfing housing 36.

Thus, in the apparatus as shown in FIG. 1, the forming drum rotates in the direction shown by Arrow B, and the scarfing roll 37 moves in the same direction of rotation, thereby providing opposed movement of the roller surface relative to the surface of the drum proximate thereto, to remove excess thickness of the laid fibrous web. Alternatively scarfing roll 37 can be rotated to provide a co-directional movement of the roller surface relative to the surface of the forming drum most proximate thereto. In either situation, the rotational speed of scarfing roll 37 should be suitably selected to provide an effective scarfing and leveling action against the contacting surface of the formed fibrous web. In like manner, any other suitable means may be employed in place of the scarfing roll assembly 35 to provide a cutting or abrading action to the laid fibrous web by relative movement between the web (forming surface) and the trimming means.

Web forming assembly 21 constitutes the outer cylindrical surface of the forming drum 18 and features a non-flow region of the foraminous forming surface which may suitably be formed by blocking plate ring 39 or other suitable means that occludes the flow of gas through the forming surface. Such occlusion serves to prevent laydown of fibers on the edges of the forming surface when the stream of air-entrained fiberized fibers is flowed thereon with passage of the entraining gas therethrough. A contoured blocking ring 39 can be configured to form a key notches 26 on the finished laid fibrous web to provide sensing point for severing of the longitudinally extending fibrous web into discrete airlaid fibrous articles. Reference has been made in the preceding sentence to a longitudinally extending character of the fibrous web 24, and this will be understood to refer to the dimension or axis of the web in the direction indicated by Arrow D, whereby the longitudinal dimension is at right angles to the transverse or lateral dimension of the web (the lateral direction hereinafter being referred to also as the cross-machine direction, in contrast to the machine direction, which is the longitudinal direction).

The details of structure of the forming drum 18 are shown in FIGS. 2 and 3, FIG. 3 being a sectional elevational view of the forming drum assembly shown in FIG. 2 taken along line 3—3 thereof. The specific structural elements shown in FIGS. 2 and 3 are numbered correspondingly with respect to the features shown in FIG. 1.

The forming drum assembly of this embodiment comprises a drum which rotates about a series of stationary baffle members which present to the foraminous forming surface, a plurality of differential pressure zones.

As shown in FIG. 3, the drive shaft 19 for the forming drum is driven in the rotational direction indicated by Arrow H by forming drum drive means 52 coupled thereto by motive power transfer means 51, which in operation may constitute a gear drive, direct shaft coupling or other suitable means. The forming drum drive shaft 19 is disposed in a journal bearing 53 which in turn is associated with a journal bearing support member 54 to provide a support structure for the forming drum in operation.

The inner housing of the forming drum includes a spindle 69 which is cylindrically concentric with the drive shaft 19 and has associated therewith spindle seals 70 which provide for pressure sealing between the front and rear lateral vacuum passages 94 and 95 and the central vacuum duct passage 93, during rotation. The drive shaft 19 is coupled to and terminates in a forming drum drive shaft spindle section 19a, which is associated with shaft seal bearings 71a and 71b and optionally with seal rings, in a manner known in the art. The forming drum assembly includes a stationary front wall 73a and a rotatable rear drum wall 74. The drive shaft 19 is secured to the rear drum wall 74 by means of a bushing and mounting assembly 75, of conventional type.

The pressure differentials imposed on the foraminous forming surface 21 are generated by means of a vacuum source (suction) means 58, such as an exhaust fan, which is coupled to the forming drum structure via vacuum transfer coupling means 59 to the air discharge (suction) duct 23. Duct 23 has associated therewith a damper assembly 60 comprising damper plate 61, and damper modulating adjustment means 62, which may be employed to manually or automatically adjust the position of the damper plate, within the annular passage as shown, both above and below the forming drum central vacuum duct 77.

The forming drum, as shown in FIGS. 2 and 3, comprises a central vacuum duct 93, the walls 77a, 77b of which at their upper ends mate with a closure flange 78, with sealing means 79 provided by radially overlapping ends of the closure flange 78 and the upper walls 77a, 77b. The forming drum as shown in FIG. 2 features a series of circumferentially spaced-apart drum wall covers 90 for entry and maintenance of the interior space and apparatus of the forming drum assembly.

The interior space of the forming drum 18 comprises a high vacuum forming zone 93 which is in the form of an arcuate segment between the duct wall baffle 102 and the duct wall baffle 103, which are shown as radially extending, imperforate plates. Circumferentially and axially adjacent to the high vacuum forming zone 93 is low vacuum pressure zone 92, 94, 95 located between chamber wall baffle 104 and chamber wall baffle 101. This low pressure zone also extends between axially spaced-apart vacuum chamber walls 73a and 77a and between chamber walls 77b and 73b at zones 94 and 95, respectively. As a result, high vacuum zone 93 is nested within and, in the shown embodiment, is surrounded on four sides by the low vacuum zone.

Intermediate the circumferentially spaced-apart chamber wall baffles 96 and 98 is an optional pressure blow-off zone 100, which receives air under pressure (from a source not shown, but which may suitably be an exhaust stream from the vacuum suction blower fan), and serves the function of imparting an air flow, under positive pressure differential from the interior to the exterior side of the forming surface 21, to assist in removal of the laid fibrous web 24. As shown, the chamber wall baffle 96 is sealed in place to the inner drum ring 99 by a seal bracket 97. The inner drum ring 99, as shown in FIGS. 2 and 3, has a plurality of openings 105 (FIG. 5) for accommodating the gas flows into, and out of, the forming drum. The inner drum ring 99 rotates in operation concurrent with the forming surface 21, to which same is attached. The inner drum ring nonetheless defines an interior region of the forming drum, which is sealed against the front and rear vacuum chamber walls 73a and 73b by closure flanges and seals analogous to flange 78 and seal 79 (as shown in FIG. 5). Between chamber wall baffle 96 and chamber wall baffle 101 is a third vacuum zone 107, and between chamber wall baffle 101 and duct wall baffle 102 is a low vacuum, passage region through which air is drawn from the scarfing zone constituted by scarfing roll assembly 35. A discrete amount of vacuum should be maintained within the third vacuum zone 107 and within the low vacuum, passage to retain the fibrous web against the foraminous forming surface 21. The discrete vacuum within these regions holds web 24 on the forming drum while the rotation of the drum transports the web toward conveyor 28.

Referring to FIGS. 4 and 5, web forming assembly 21 is distinctively configured in multiple layers to efficiently produce a laid-fibrous web. The outermost portion of web forming assembly 21 is comprised of a foraminous web forming layer 122 upon which the fibers of web material are deposited. A foraminous spacing means, such as one comprised of spacing members 120 and 121, is located downstream from web forming layer 122 in an adjacent, radially inward position to support the web forming layer. A foraminous gas flow regulating layer 135 is in turn located downstream from and adjacent to the spacing means to provide a selected pattern of gas flow through web forming layer 122.

The regulating or attenuating layer 135 is positioned in closely spaced registration with, and transverse to flow of gas through the forming surface to diminish the pressure differential exerted on the forming surface in register with the vacuum attenuating plate.

Figure 6A:
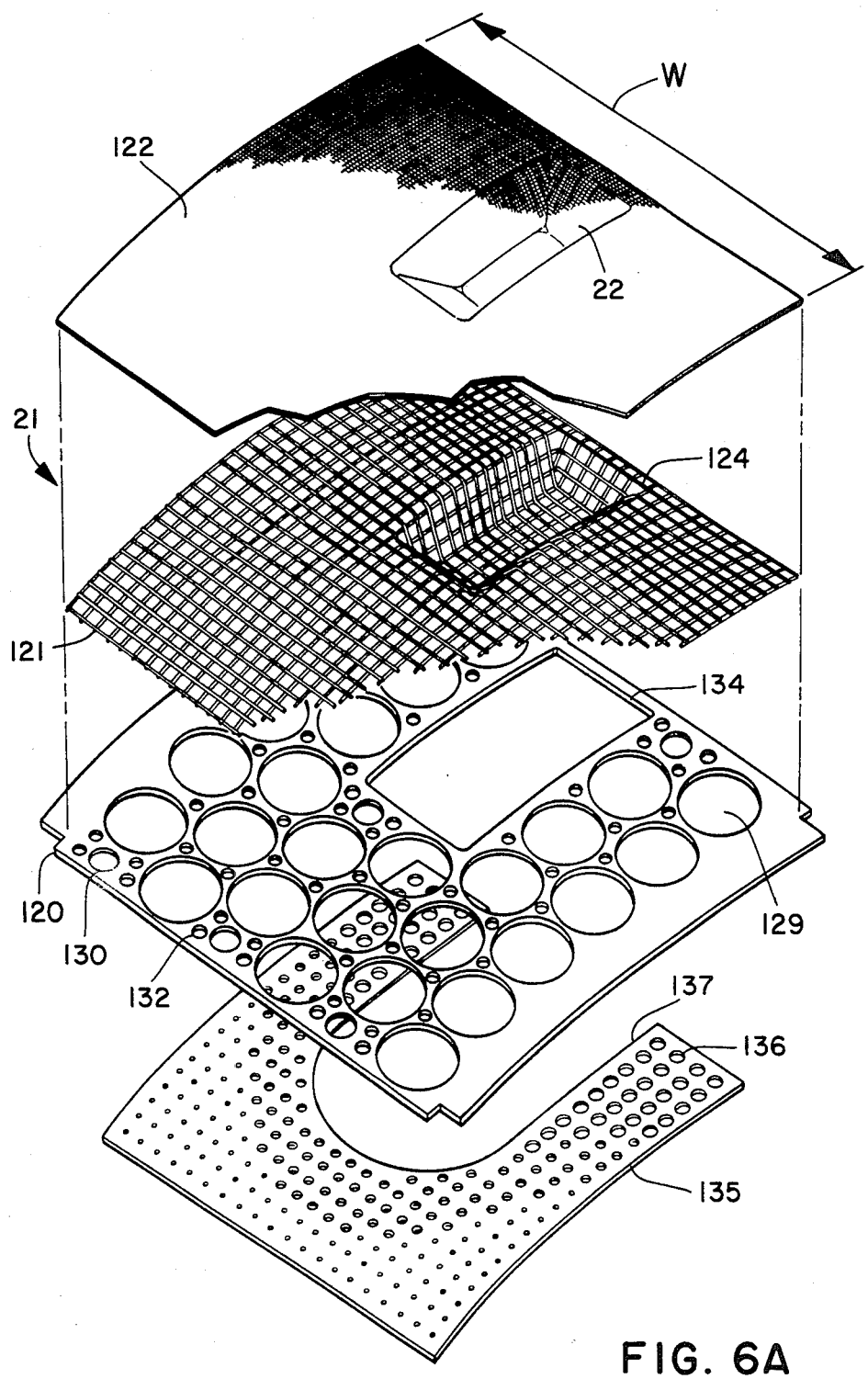
FIGS. 6A and 6B representatively show an exploded, perspective views of the multi-layer forming assembly of the forming drum.

The forming surface, as shown, is thus made up of a series of circumferentially extending and radially adjacent elements. In the aggregate, these elements form an air-laid web forming path having a width W (FIG. 6A) and extending around the entire peripheral cylindrical surface of the forming drum. In particular aspects of the invention, the web forming assembly can advantageously be configured to produce a web having a greater basis weight of fibrous material in selected medial portions than in its marginal edge portions. For example, FIGS. 5 and 6A illustrate an embodiment of the invention in which the web forming assembly includes at least one pocket recess 22 for forming a higher basis weight, medial portion in web 24. In the embodiment illustrated in FIG. 1 the foraminous web forming assembly 21 includes a plurality of circumferentially spaced-apart, centrally (in the cross-machine direction) aligned, concavely contoured surface portions (pocket recesses) 22 formed thereon.

Figure 6B:
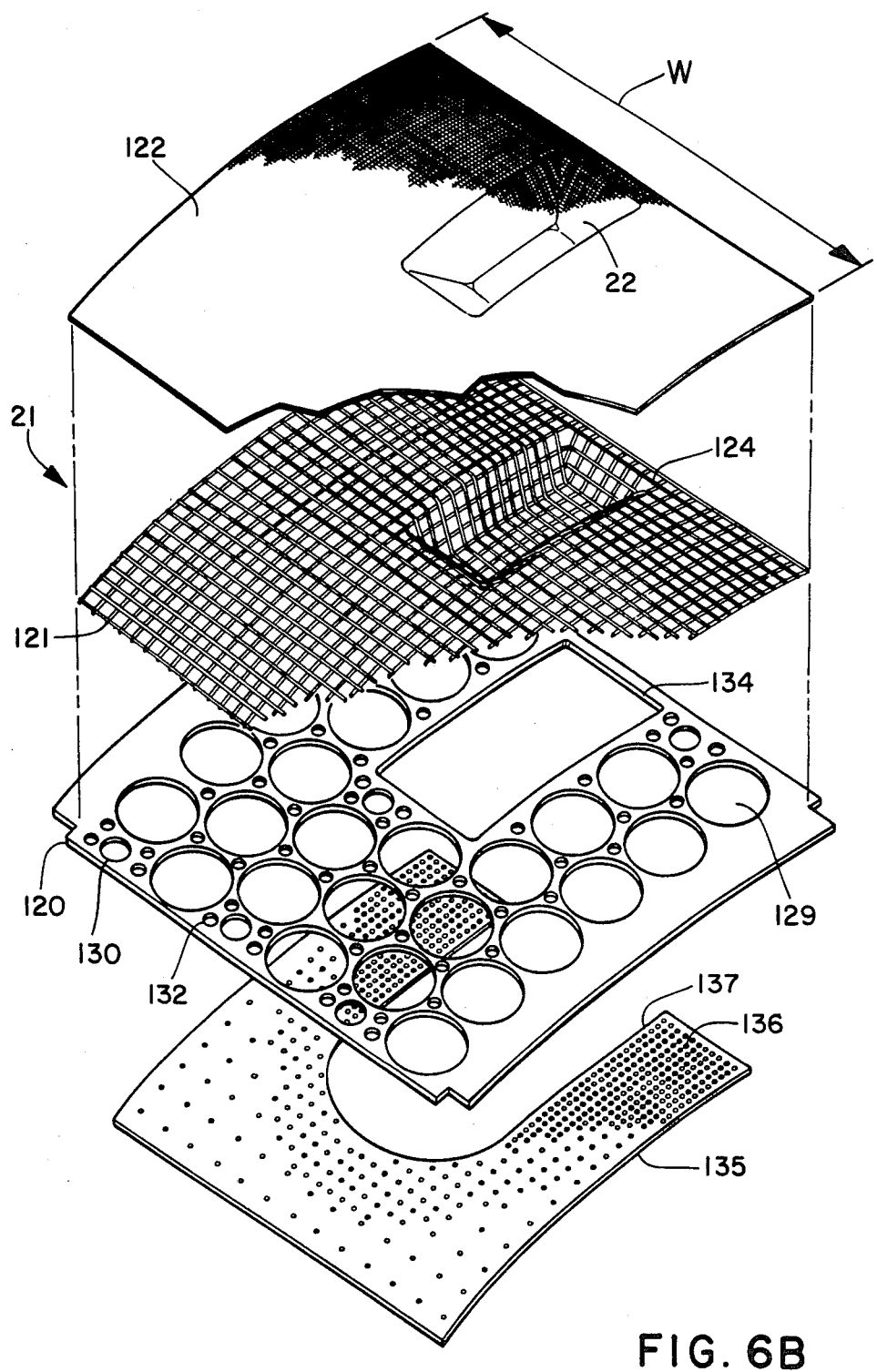
Figure 6C:
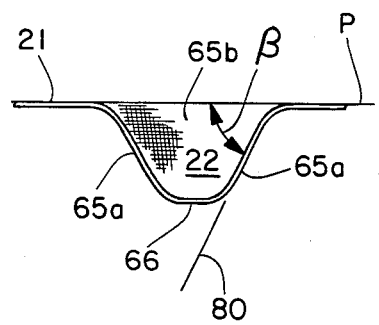
FIGS. 6C and 6D show cross-sectional views of a representative pocket recess.
Figure 6D:
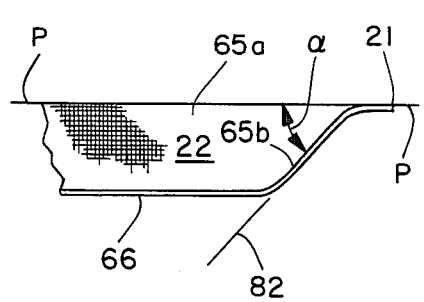

As representatively shown in FIGS. 6A, 6C and 6D, concavely contoured surface portions 22 are bounded by longitudinal side wall members 65a, transverse end wall members 65b, and a generally planar base wall member 66 which is disposed at least approximately parallel to the plane of the adjacent portion of foraminous forming assembly 21. The longitudinal side wall members 65a and transverse end wall members 65b are angularly oriented with respect to the plane of the forming assembly 21 proximally adjacent the concavely contoured surface portion 22, to define an included angle therebetween of not more than about 70°. Preferably this included angle is from about 45° to 68°. Thus, the included angle between respective longitudinal side wall members 65a and the plane P of the portion of forming assembly 21 which is proximally adjacent thereto is measured by the angle beta in FIG. 6C. Similarly, the included angle between respective transverse end wall members 65b and the plane P of the portion of forming surface proximally adjacent thereto is measured by the angle alpha in FIG. 6D.

The side wall angle, beta, is measured between the side wall surface (extending by straight line 80 in FIG. 6C) and the plane P of the forming surface proximally adjacent the concavely contoured surface portion 22. As used herein, the term "forming surface proximally adjacent the concavely contoured surface portion" refers to the surface portion of assembly 21 that is adjacent to the concavely contoured surface portion 22 but is not in any way deformed as part of or an extension of the contour of the concave surface portion 22. The term "concavely contoured" as used in such context refers to the fact that the forming surface has a depression therein which under air-laying fiber deposition conditions will result in the formation of a protrusional area on the air-laid fibrous web. In like manner, as shown in FIG. 6D, the end wall member 65b has an angle of orientation, alpha, which is measured between the end wall member 65b (extending by straight line 82) and the plane P of the forming surface proximally adjacent the concavely contoured surface portion.

In the present invention, the wall angles alpha and beta should each be not more than about 70°, and preferably, should each be in the range of from about 45° to 68° to effect improved releasability of the fibrous web from the forming surface. The angles alpha and beta may be, but need not be, identical. For example, good releasability characteristics have been obtained in practice where the angle beta is approximately 65° and the angle alpha is approximately 45°, with the concavely contoured surface portion 22 being of generally inverted frusto-pyramidal shaped. Nonetheless, it is to be recognized that numerous other shapes and conformations for the concavely contoured surface portion may be employed to good advantage, other than the generally inverted frusto-pyramidal shape of elongate form which is shown in the illustrative drawings. For example, conical or oblate conical openings could be employed, in addition to any other wall shapes and orientations meeting the side wall angle criteria hereof.

In the specific embodiment shown in the drawings, wherein the concavely contoured surface portion 22 is elongate in shape and its bounding walls comprise longitudinal side wall members 65a and transverse end wall members 65b joined at their bottom edges to a base wall member 66, it is preferred that the included angles beta of the longitudinal side walls 65a are between about 55° and 68° and the included angles alpha of the transverse end walls 65b are between about 45° and 60°.

In a particular embodiment of the invention, web forming layer 122 is, for example, comprised of a metallic wire screen mesh formed with a substantially square or rectangular grid pattern. The wire size of the mesh is about 33 gauge (about 0.03 cm in diameter), and the openings between the wires measure about 0.05 cm across. The wire size and opening sizes can be varied as desired. However, the openings should not be so small that they become plugged by fibers and excessively restrict the air flow therethrough. Neither should the openings be so large that they allow excessive amounts of fibers to pass through the screen and delay the formation of web 24.

To provide a fibrous web having a contoured basis weight, web forming layer 122 optionally includes at least one pocket recess 22 formed therein. (FIGS. 5 and 6A) Pocket recess 22 allows an accumulation of a greater basis weight of fiber material in a restricted medial portion of web 24. In addition, pocket 22 advantageously allows a generally sideways gas flow through the side walls of the pocket to increase the rate of accumulation of the fiber material within the pocket. To provide an increased production rate, a plurality of substantially regularly spaced pocket recesses are formed along the circumferential length of web forming layer 122.

The embodiment of the foraminous spacing means shown in FIG. 4 is, for example, comprised of hardware cloth 121 and spacer sheet member 120. Hardware cloth 121 is a coarse wire mesh formed with a generally square or rectangular grid pattern. The wire size is about 18 gauge (about 0.12 cm diameter) and openings between the consecutive wires measure about 1.15 cm across. Hardware cloth 121 positions web forming layer 122 away from spacer sheet member 120 by a discrete distance while allowing a substantially unrestricted and substantially uniform flow of air from web forming layer 122, around and through the wire structure of hardware cloth 121 and then into spacer sheet member 120. The generally circular cross-section of the wire minimizes the contact area between web forming layer 122 and hardware cloth 121. Similarly, the rounded cross-section of the wire minimizes the contact area between hardware cloth 121 and spacer sheet member 120. This very small contact area with hardware cloth 121 prevents excessive restriction of the gas flow from web forming layer 122 into spacer sheet member 120. Hardware cloth 121 also helps to support web forming layer 122 and reduce distortions thereof.

In the particular embodiment of the invention shown in FIG. 5 and 6A, hardware cloth 121 has a contoured spacer pocket 124 formed therein. Spacer pocket 124 is configured and sized to accommodate the placement of forming pocket 22 therein and to help support the mesh material employed to construct the forming pocket. The resultant support provided by spacer pocket 124 in hardware cloth 121 helps to reduce distortions of forming pocket 22 in forming layer 122.

Spacer sheet member 120 is constructed from a substantially rigid sheet of material, such as metal, which is about 0.3 cm thick. The spacer sheet member is suitably contoured to conform to the cylindrical shape of forming drum 18, and has a plurality of openings 129-132 formed therethrough to allow a substantially unrestricted air flow from hardware cloth 121. These openings range from about 0.6-6.4 cm in diameter. In the shown embodiment, larger openings 129 measure about 5.8 cm in diameter and smaller openings 130-132, which are located intermediate the regions defined by the large openings, measure about 0.6-2.6 cm in diameter. In addition, spacer sheet member 120 has a cut-out opening 134 which is configured to accommodate placement of forming pocket 22 and spacer pocket 124 therethrough.

In the embodiments shown in FIGS. 4, 5 and 6A, gas flow regulating layer 135 contacts the side of spacer sheet member 120 located opposite to the side contacted by hardware cloth 121. Regulating layer 135 is comprised of a foraminous layer composed of a suitable material such as sheet steel. The regulating layer has a selected pattern of openings formed therethrough to produce a predetermined pattern of gas flow through web forming layer 122. In addition, regulating layer 135 has a selectively contoured portion 137 which is configured to skirt around the marginal boundary of forming pocket 22. More particularly, the vacuum attenuating plate can have an opening or hole therethrough which is sized and configured to accommodate the placement of the concavely contoured surface portion therein. Alternatively, the vacuum attenuating plate may, as shown in FIG. 6A, be generally U-shaped with its inner edge circumjacent to bounding walls of the concavely contoured surface portion.

To establish the predetermined pattern of air flow through web forming layer 122, regulator layer 135 has regulator openings 136 which can be selectively configured and varied. More particularly, regulating layer 135 can have larger size openings in those selected areas or zones wherein a greater basis weight of fiber material is to be deposited on web forming layer 122. Similarly, regulating layer 135 can have smaller sized openings in those regions wherein a lower basis weight of material is to be deposited on the web forming layer (FIG. 6A). In an alternate configuration, the openings through regulating layer 135 can all be substantially of the same size. A greater density of openings would be located in those selected regions where a greater basis weight of fiber material is to be deposited (FIG. 6B). A combination of these two techniques may also be employed.

The component elements of web forming assembly 21 are preferably assembled and held together by suitable fastening means. For example, web forming layer 122 can be soldered to hardware cloth 121, and the hardware cloth may be spot welded to spacer sheet member 120.

Figure 7:
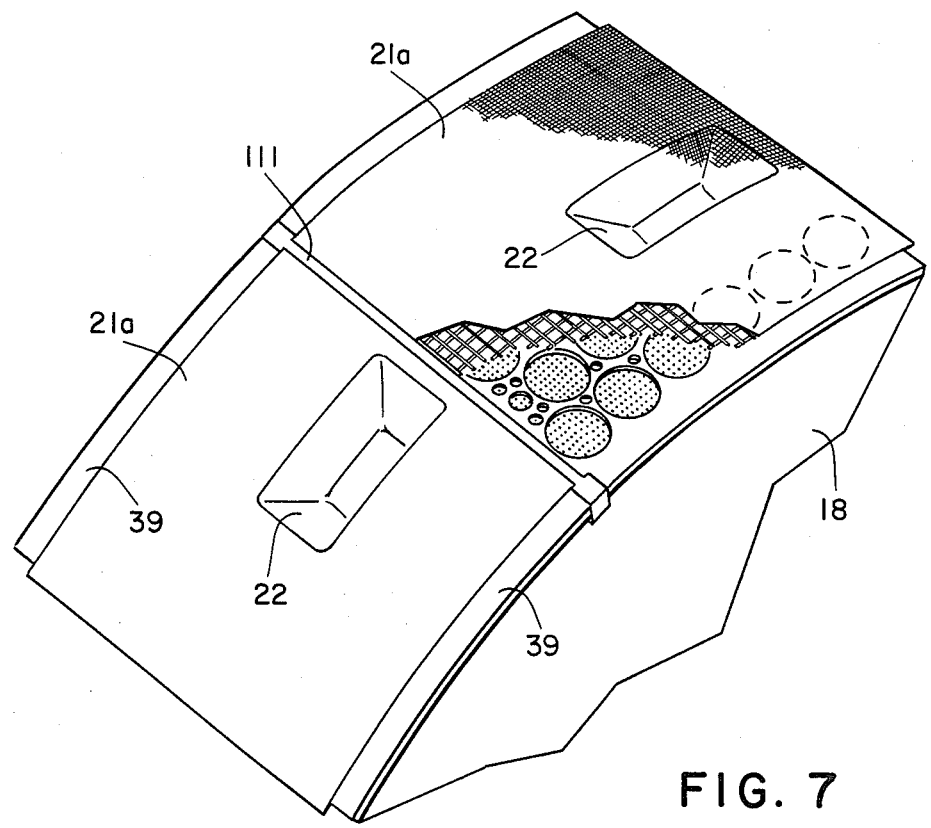
FIG. 7 representatively shows a forming drum having a plurality of web forming assembly segments.

Referring to FIG. 7, web forming assembly 21 is suitably constructed and arranged to be fit upon drum 18. For example, web forming assembly 21 can be configured as a plurality of assembly segments 21a, which are sequentially and adjacently placed along the circumferential periphery of forming drum 18. The individual assembly segments are readily installed and replaced from the outside, upstream region of drum 18, and as a result, the web forming assembly can be quickly reconfigured to produce a variety of article types. For example, the web forming assembly of the invention can be efficiently reconfigured to produce absorbent pads having different basis weight contours or different sizes by removing one set of segments 21a and replacing them with another, differently configured set of segments.

The web forming assembly is connected to forming drum 18 by suitable fastening means. In the embodiment shown in FIG. 3, web forming assembly 21 rests on drum flange members 140 which position and support the web forming assembly relative to chamber wall 73a and drum side wall 74. Flange members 140 are fixedly mounted relative to drum side wall 74 and extend circumferentially around the drum. Holding means, such as screws and retainer (blocking) rings 39, hold web forming assembly 21 substantially fixed against drum flange members 140.

The embodiment of the invention shown in FIGS. 1-3 includes a rotatable cylindrical drum the outer circumferential wall surface of which comprises the web forming assembly. A plurality of concavely contoured forming surface portions 22 are circumferentially spaced apart thereon, and a plurality of radially extending, stationary baffles and walls are disposed in the interior of the rotatable cylindrical drum. These walls and baffles divide the interior into plural arcuate segments which communicate with respective differential pressure zones on the forming surface. A pneumatic flow means defines pressure differential zones on the forming surface and imposes a pressure differential thereon. The pneumatic flow means comprises a vacuum suction means joined in gas flow communication with a first arcuate segment in the cylindrical drum. The first arcuate segment defines a vacuum laydown zone on the forming surface, and the vacuum suction means draws air through the vacuum laydown zone on the forming surface, into the first arcuate segment and out of the rotatable cylindrical drum. Such apparatus can further comprise means for diverting a portion of the flow of air drawn through the vacuum laydown zone on the forming surface into the first arcuate segment, under positive pressure into a second arcuate segment defining a pressurized take-off zone for removal of the laid fibrous article from the forming surface.

As shown in FIGS. 2 and 3, the walls 77a, 77b bound the generally wedge shaped, central duct 91, which forms the high vacuum forming zone 93 constituting an arcuate segment of the rotatable cylindrical drum. The walls are of arcuate shape and are disposed in transversely spaced relationship to one another to divide the first arcuate segment into transverse subsegments 94, 93 and 95 defining corresponding vacuum laydown subzones on the forming surface. Flow restriction means comprised on the damper assembly 60 is interposed between the vacuum suction means 58 and the two outer vacuum laydown subzones of the forming surface, 94 and 95, for effecting a transversely varying differential pressure on the forming surface vacuum laydown zone, whereby the laid fibrous article has a transversely varying basis weight (i.e., in the cross-machine direction).

In contrast to the specific embodiment shown in FIG. 3, wherein the respective front and rear walls of the central vacuum duct 91 (arcuate walls 77a and 77b) transversely divide the vacuum laydown zone into differential pressure subzones, it may be suitable in other applications of the present invention to utilize a greater or lesser number of arcuate baffles to define a correspondingly greater or lesser number of transverse subzones of the forming surface, in combination with flow restriction means disposed between the forming surface subzones and the vacuum suction means in correspondingly greater or lesser numbers, but in all instances where such cross-machine basis weight differential of the laid fibrous web is desired, flow restrictions will be interposed between at least one of the forming surface vacuum laydown subzones and the suction means. Alternatively, in some instances of the present invention, it may be desirable to provide a corresponding variation of basis weight in the formed fibrous article with the highest basis weight in the outer longitudinal sections of the fibrous web, and accordingly flow restriction means may be associated with the central gas flow passage to provide a reduced longitudinally extending central basis weight region relative to the outer longitudinally extending regions of the fibrous web corresponding to the peripheral gas flow passages. In the FIG. 3 apparatus, the flow restriction means, in the form of a damper assembly 60 have been disposed between the transversely outer forming surface laydown subzones and the vacuum suction means.

In operation, the air-laid fibrous web is formed from a stream of air-entrained fiberized fibers, by flow of the entrainment gas through the openings in the foraminous forming assembly 21 and into the chambers constituting the vacuum forming zones 92-95 in the rotatable drum 18. Suction is also applied to the resulting laid fibrous web in the vicinity of a scarfing zone defined by the scarfing roll assembly 35 and the scarfing housing 36.

In a particular aspect of the invention, chamber wall member 101 is selectively moveable within forming drum 18 along the circumferential direction thereof. The movement of wall member 101 can advantageously be employed to regulate the amount of vacuum applied to the drum-side surface of the portion of fibrous web 24 which is located in the scarfing zone under housing 36. For example, with respect to FIG. 2, a clockwise repositioning of wall member 101 would decrease the amount of vacuum applied to the fibrous web, and a counter-clockwise repositioning of the wall member would increase the amount of vacuum applied to the fibrous web. If an excessive amount of vacuum is applied to the portion of web 24 within the scarfing zone, the fibrous material trimmed away by the scarfing roll can be redeposited onto the web instead of being withdrawn out of housing 36.

The inflows of air to the arcuate segment constituting high vacuum forming zone 93 and the low vacuum zone 92, 94, 95 are exhausted from the forming drum in air discharge duct 23, under the influence of vacuum suction by vacuum means 58. Concurrently, the drum rotates to pass the air-laid fibrous web on the forming surface from the vacuum laydown zone to the scarfing zone where excess thickness of the fibrous web is trimmed to a predetermined extent, following which the air-laid fibrous web moves past the intermediate vacuum zone 107 (FIG. 2) and finally to an optional pressure blowoff zone 100. In blowoff zone 100, air is introduced under pressure and directed radially outwardly against the fibrous web on the forming surface portion circumferentially aligned therewith, whereby the gas pressure and the specifically contoured surface portion 22 effects a ready release of the fibrous web from the forming surface, without binding or sticking of the air-laid fibrous web in the depressions 22, such as would adversely impact the normal operation of the apparatus, and potentially necessitate shut-down and manual removal of the fibrous web from the forming surface. In an alternative configuration of the apparatus of the invention, a vacuum suction box 116 can be located below conveyor belt 28 to help remove web 24 from the forming surface 21. Vacuum box 116 opens onto belt 28, and a suction of air out of the vacuum box through outlet opening 118 draws an air flow through perforations in the conveyor belt. This flow of air, in turn, operates to draw web 24 away from the forming surface. Vacuum box 116 can be employed with or without the use of positive pressure in blowoff zone 100.

The annular space between the inner ring 99 and the forming surface 21 is circumferentially sealed by various circumferentially spaced, radially sealing members to preserve the pressure differentials in the various differential pressure zones of the forming assembly. More particularly, a plurality of transverse sealing members 110 connect in sealing engagement between inner ring 99 and forming surface 21, and also connect in sealing engagement between drum walls 73a and 74. These transverse sealing members substantially prevent the movement of ambient air through the annular space between inner ring 99 and forming surface 21 and into the low and high vacuum zones.

To better segregate the high vacuum zone from the low vacuum zone, circumferential sealing members 112 can optionally be located in the annular space between inner ring 99 and forming surface 21. Pairs of sealing members 112 are axially spaced apart and are located adjacent to both longitudinal side wall members of the contoured surface depressions 22. The circumferential sealing members connect in sealing engagement with transverse sealing members 110 and operate to reduce cross flow between the high vacuum zone and the low vacuum zone along a path through the annular space.

To further reduce the intrusion of ambient air into the differential vacuum zones, sealing flange members 114 are connected to chamber wall baffles 101 and 104, and are arranged to contact inner ring 99 with a slideable, sealing engagement. Flange members 114 extend axially across the width dimensions of chamber wall baffles 101 and 104, and have a circumferentially extending length dimensions which are at least equal to the circumferential distance between consecutive transverse sealing members 110. The above-mentioned length dimensions refer to the portions of flange members 114 that slideably contact ring 99. As illustrated in FIG. 2, the slideable portions of flange members 114 are arranged to extend circumferentially away from housing 11. Thusly configured, flange members 114 substantially prevent the intrusion of ambient air along a path that extends through ring 99, around the edge of transverse sealing member 110, back through ring 99, around the edge of chamber wall baffle 101 or 104, and back again through ring 99 into the vacuum zones.

FIG. 8 shows a plan view of a laid fibrous article, which is formed by the apparatus illustrated in FIGS. 1-5. This fibrous article is particularly suitable for use in a disposable diaper. The air-laid article is shown in the drawing as referenced to the width W of the air-laid web forming path 140 and the vacuum regulating layer 135, the profiles of which are shown in dotted line representation for ease of reference. The air-laid fibrous web article 150 is shown with a lateral center line X-X, and is formed from the longitudinally extending web 24 as shown in FIG. 1, by severing the web 24 transversely into suitable lengths, as described hereinafter in greater detail. The fibrous web article 150 has a rear section 151, posterior to the center line X-X and a front section 152 anterior thereto. As mentioned previously this fibrous web article features leg cut-outs defined by edges 153, 154, resulting from the utilization of the arcuate blocking plates 40 as shown in FIG. 1. The key notch 26 formed by the non-flow region associated with blocking plate 39 in FIG. 1 is located at a side edge of the front section of the fibrous web article; an alternative position for the open area is shown at 26'. Such notch or "key" can be employed as a reference point for severing the longitudinally extending fibrous web into lengths of predetermined dimension.

The longitudinal central zone L of the fibrous web article provides a higher basis weight region of the article relative to zones M and N on either side thereof. The respective lines Y and Z demarcating the successive longitudinal zones define the general, approximate locations of fold-lines, along which the fibrous web article may be folded for storage and packaging purposes. The longitudinal peripheral zones correspond to the outer forming surface subzones overlying vacuum passages 94 and 95 as shown in FIG. 8, with the central longitudinal zone L corresponding to vacuum passage 93 in FIG. 8.

Each of the longitudinal peripheral zones M, N has associated therewith laterally extending corner segments or "ears" with the front section 152 having left-hand and right-hand ears, 157 and 158 respectively, with rear section 151 having associated therewith corresponding ears 159 and 160. Positioned in the central longitudinal zone L of the front section 152 is an integral pad 25, corresponding to the protrusion formed on the longitudinal extending web in the operation of the apparatus shown in FIGS. 1-5. Pad 25 comprises a frusto-pyramidal, nonseparable protrusion from the fibrous article's top surface, corresponding to the concavely contoured surface portion of the forming surface. Pad 25 features a pad top surface 165 which is radiused and corresponds to the base wall member 66 of the forming surface 21. The pad side surfaces 166 and 167 correspond to the side walls of the concavely contoured surface portion, and the pad end surfaces 168, 169 correspond to the end wall members of the concavely contoured forming surface portion.

A high basis weight region 175 extends transversely across the longitudinal zones M, L and N generally in the front section of the fibrous web article, and its boundary is demarcated by and corresponds to the edge 176 of the vacuum blocking plate 135, whereby the basis weight of the material surrounding pad 25 is higher than the ear regions 157, 158 in the front section of the fibrous article and is higher than the basis weight of the rear section 151 of the fibrous article, with the exception of the small arcuate segment extending centrally longitudinally for a short distance posterior of the lateral center line X-X.

In the preferred practice of the present invention, the vacuum laydown zone has subzones which are situated and arranged to provide a lower pressure differential in the peripheral forming surface subzones defined by vacuum passages 94, 95 relative to the central subzone 93, and the blocking plate is configured to provide approximately 65% of the weight of the fibrous article in the front section 152 of the laid article and approximately 35% of the weight in the rear section 151 thereof. Such a fibrous article is highly advantageous in disposable diaper service.

It will be readily apparent that various conventional devices and techniques can be employed to sever fibrous web 24 into predetermined lengths to provide selected laid fibrous articles. For example, conventional knives or cutter mechanisms may be employed.

In another embodiment of the invention, discrete fibrous articles can be directly formed on forming assembly 21. As representatively shown in FIG. 7, a plurality of blocking bar members 111 can be located at selected locations along the circumference of the forming surface. Bar members 111 interconnect between blocking rings 39 and are generally aligned along the axial dimension of forming drum 15. These bar members also overlie forming surface 21 and block the accumulation of fibers along relatively narrow, transverse portions of the forming surface. As a result, the deposition of fibers onto forming surface 21 can create a substantially non-continuous web comprised of individual, discrete fibrous articles.

In a particular aspect of the invention, fiber forming chamber 11 includes fiber directing means, such as baffle plates 144 which steer and direct fibers toward the middle portion of web forming assembly 21, as representatively shown in FIG. 3. As a result, a greater quantity of fibers deposit onto the middle portion of web forming assembly 21 and more readily fill in the pocket portions of the forming assembly, particularly the forming pocket 22 in web forming layer 122.

Figure 9:
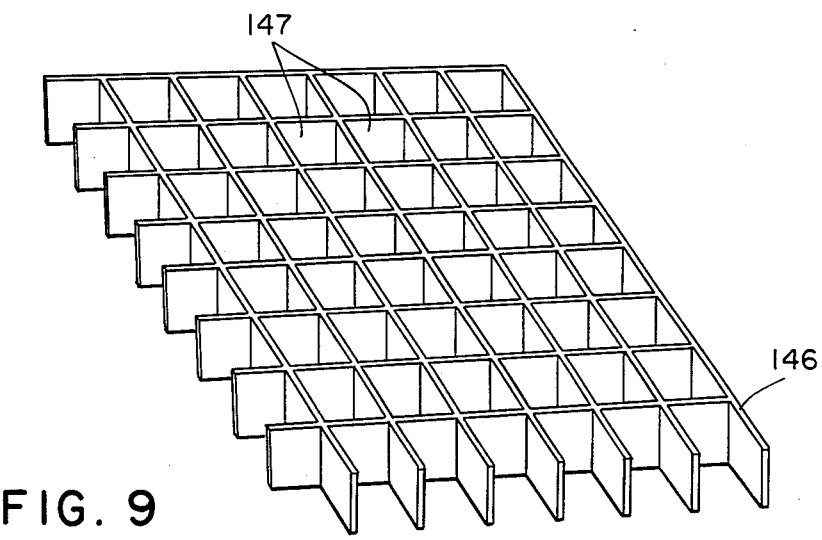
FIG. 9 representatively shows a spacing member having a sheet-like grid configuration.

In another aspect of the invention shown in FIG. 9, the spacing member can alternatively be comprised of a sheet-like grid 146, such as a honeycomb type grid or a grid with other polygonal patterns or curvilinear patterns. Preferably, grid sheet member 146 is sufficiently deformable to follow the curvilinear path of a forming drum or of a endless forming belt. The sheet structure of grid 146 would have sufficient thickness to suitably space web forming layer 122 at a operable distance from regulating layer 135. Also, the edges of the grid elements which contact web forming layer 122 would be suitably rounded or otherwise contoured to allow a substantially unrestricted gas flow into the grid structure from the region immediately adjacent to and downstream from the web forming layer. These grid elements would define a plurality of individual conduit cells 147 that would direct air flow from web forming layer 122 to regulating layer 135 and would substantially span across the distance between the web forming layer and the regulating layer.

Figure 10A:
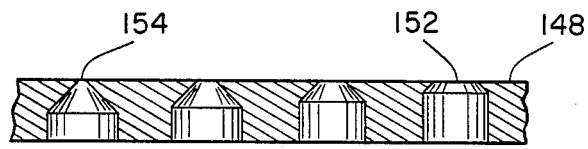
FIGS. 10A-C representatively show flow regulating members having tapered openings formed therein.
Figure 10B:
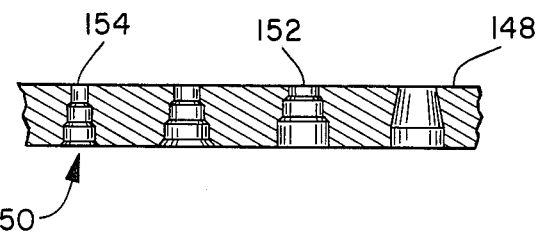
Figure 10C:
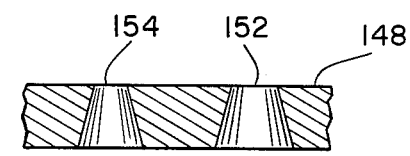

In a further aspect of the invention, the flow regulating layer can be comprised of a sheet-like member 148 which has a plurality of selectively "tapered" openings formed therethrough. Examples of tapered holes are illustrated in FIGS. 10A-C, and may be formed with suitably contoured machining or drilling tools. For example, a sequence of drills having increasing diameters can be employed to form a stepped hole, as representatively shown in FIG. 10B. This stepped hole 150 can provide an effective tapered opening. Sheet layer 148 can, for example, be combined with a suitable hardware cloth spacing means to allow a substantially unrestricted gas flow from the region immediately adjacent to and downstream from the associated web forming layer. Tapered openings or holes 152 and 154 are configured with selected diameters and angles of taper, and are arranged with the smaller sized end of the hole more proximate to the hardware cloth and with the larger sized end of the hole more distant from the hardware cloth. This arrangement can reduce plugging of the holes by the fibers of web material. Holes 152 located at regions where a greater basis weight of material is desired would have a more open taper to provide less restriction to the gas flow. In contrast, holes 154 located at regions where a lower basis weight of material is desired would have a more closed taper and would provide more restriction to the flow of gas. In this particular embodiment of the invention, sheet member 148 effectively performs the functions of both the spacing member 120 and the flow regulating layer 135 shown in FIG. 6A.

The following example is given to provide a more detailed understanding of the invention. The materials, proportions and other parameters are exemplary and are not intended to specifically limit the invention.

EXAMPLE

A forming drum was constructed in accordance with FIGS. 1, 2 and 3, and a web forming assembly was constructed in accordance with FIGS. 5 and 6A. Drum 18 had a diameter of 57.85 in (146.9 cm) and rotated at 20 rpm. Suction pump fan 58 drew air out from duct 92 at a rate of 4.72 m$^3$/sec, and a fiberizer provided fibrous web material at a rate of 12 kg/min. The web material was composed of wood pulp fibers.

Web forming layer 122 was constructed from 28×30 mesh wire screen. The wire diameter was 0.03 cm and the openings through the screen measured 0.05 cm across.

Hardware cloth 121 was a wire screen having ½ in (1.27 cm) square mesh openings. The wire diameter was 0.12 cm and the openings through the screen measured 1.15 cm across.

The forming pocket 22 had a generally frusto-pyramidal shape that was 4.7 cm deep and measured 19 cm×8.98 cm at its base. Spacer pocket 124 has a shape similar to that of forming pocket 22 but was suitably sized to accommodate the placement of the forming pocket therein.

Spacer sheet member 120 was fabricated from sheet steel and was 0.3 cm thick. The large holes 129 measured 5.56 cm in diameter and were substantially uniformly distributed across the surface of the sheet member. Smaller holes 130 and 132 were located in the areas between the large holes. Holes 130 measured 2.6 cm in diameter and holes 132 measured 0.95 cm in diameter.

Cut-out 137 was sized and configured to accommodate the placement of forming pocket 22 and spacer pocket 124 therethrough.

Flow regulating layer 135 was composed of 24 gauge stainless steel sheet, and had an edge 137 which was configured to skirt around the region of forming pocket 22. Regulating holes 136 formed through the regulating layer measured 0.31 cm in diameter and were distributed across the layer in a straight centered pattern.

The apparatus was employed to form a fibrous web 24 which had an alternating pattern of high basis weight zones and low basis weight zones. Web 24 was cut into individual pads each of which had a medial portion with a basis weight of 0.16 g/cm$^2$ and edge portions with a basis weight of 0.03 g/cm$^2$. These pads were employed in the manufacture of disposable diapers for infants.

Having described the invention in rather full detail, it will be readily apparent that various changes and modifications can be made without departing from the spirit of the invention. Such changes and modifications are all contemplated as being within the scope of the invention as defined by the subjoined claims.

I claim:

1. An apparatus for forming a fibrous web, comprising:
   a. a foraminous web forming layer for receiving a deposit of fibers of web material thereon;
   b. foraminous spacing means for supporting said web forming layer while allowing a substantially unrestricted gas flow from a region immediately adjacent to and downstream from said web forming layer; and
   c. a gas flow regulating layer, which has a selected pattern of apertures therethrough and is fixedly positioned in adjacent facing relation with said foraminous spacing means, for providing a selected pattern of gas flow through said web forming layer, wherein said web forming layer, said foraminous spacing means and said gas flow regulating layer are constructed to form a replaceable, web forming assembly.

2. An apparatus as recited in claim 1, wherein said foraminous web forming layer has a pocket recess formed therein.

3. An apparatus as recited in claim 2, wherein said gas flow regulating layer has an opening configured to skirt around selected edges of the pocket recess in said web forming layer.

4. An apparatus as recited in claim 2, wherein said pocket recess in said web forming layer is contoured to have a selected cross-sectional shape.

5. An apparatus as recited in claim 2, wherein said foraminous web forming layer has a pocket recess formed therein and said foraminous spacing means has a contoured edge portion which accommodates the positioning of the pocket recess of said web forming layer.

6. An apparatus as recited in claim 1, further comprising transport means for moving said web forming layer, said spacing means and said flow regulating layer.

7. An apparatus as recited in claim 6, wherein said foraminous web forming layer, said foraminous spacing means and said gas flow regulating layer are constructed to form an assembly which is installable onto an outside portion of said transport means.

8. An apparatus as recited in claim 6, wherein said transport means is comprised of a rotatable drum which is connected to move said web forming layer, said spacer means and said regulating layer upon a peripheral rim section of said drum.

9. An apparatus as recited in claim 6, wherein said transport means is comprised of an endless belt mechanism upon which said web forming layer, said spacer means and said regulating layer move.

10. An apparatus as recited in claim 1, further comprising:
fiber supply means for providing said fibers of web material; and
flow forcing means for providing a flow of gas through said web forming layer.

11. An apparatus as recited in claim 1, wherein said foraminous spacing means comprises:
a. a hardware cloth mesh which is located downstream and adjacent to said web forming layer; and
b. a spacer sheet member, which is located downstream and adjacent to said hardware cloth mesh and has a plurality of openings formed therethrough.

12. An apparatus as recited in claim 1, wherein further comprising baffle means for directing said fibers of web material toward selected areas of said foraminous web forming layer.

13. An apparatus as recited in claim 12, wherein said baffle means is configured to direct a greater amount of said web material fibers toward a center portion of said foraminous web forming layer than toward marginal edge portions thereof.

14. An apparatus as recited in claim 1, further comprising a web shaping means for leveling a top free surface of said formed fibrous web.

15. An apparatus as recited in claim 14, wherein said shaping means is comprised of a scarfing roll.

16. An apparatus as recited in claim 1, wherein said gas flow regulating layer is comprised of layer of material having a selected areal pattern of tapered holes formed therethrough, wherein said tapered holes are positioned with the smaller sized opening portions thereof facing toward said web forming layer.

17. A method for forming a fibrous web, comprising the steps of:
a. depositing fibers of web material on a foraminous web forming layer by impinging a stream of gas-extrained fibers on said web forming layer while passing the gas component of said stream through said web forming layer;
b. supporting said web forming layer with a foraminous spacing means to reduce distortions in said layer while depositing said fibers and while allowing a substantially unrestricted flow of said gas through said spacing means; and
c. allowing said gas to flow through a gas flow regulating layer, of which has a selected pattern of apertures therethrough and is fixedly positioned in adjacent facing relation with said supported web forming layer, thereby providing a selected pattern of gas flow through said web forming layer;
d. said web forming layer, said foraminous spacing means and said gas flow regulating layer being constructed to form a replaceable web forming assembly.

18. A method as recited in claim 17, further comprising the step of moving said web forming layer.

19. A method as recited in claim 17, wherein said supporting step (c) includes the steps of:
a. locating a hardware cloth mesh downstream and adjacent to said web forming layer; and
b. locating a spacer sheet member having a plurality of openings formed therethrough downstream and adjacent to said hardware cloth mesh.

20. A method as recited in claim 17, further comprising the step of directing said fibers of web material toward selected medial areas of said foraminous web forming layer.

21. A method as recited in claim 17, further comprising the step of leveling a top free surface of said formed fibrous web.

22. A method as recited in claim 21, wherein said leveling step includes the step of leveling with a scarfing roll.

23. An apparatus for forming a fibrous web, comprising:
a. a foraminous web forming layer for receiving a deposit of fibers of web material thereon;
b. foraminous spacing means for supporting said web forming layer, said spacing means having rounded support edges which minimize an area of contact with said web forming layer and thereby allow a substantially unrestricted gas flow from a region immediately adjacent to and downstream from said web forming layer; and
c. a gas flow regulating layer, which has a selected pattern of apertures therethrough and is positioned in adjacent facing relation with said foraminous spacing means, for providing a selected pattern of gas flow through said web forming layer, wherein said web forming layer, said formaminous spacing means and said gas flow regulating layer are constructed to form a replaceable, web forming assembly.

24. An apparatus as recited in claim 23, further comprising a rotatable drum which is constructed to move said web forming layer, said spacer means and said regulating layer upon a peripheral rim section of said drum.

25. An apparatus as recited in claim 24, wherein said foraminous spacing means comprises:
a. a hardware cloth mesh which is located downstream and adjacent to said web forming layer; and
b. a spacer sheet member, which is located downstream and adjacent to said hardware cloth mesh and has a plurality of openings formed therethrough.

26. An apparatus as recited in claim 24, wherein said spacing means comprises a sheet-like, grid member having sufficient thickness to space said web forming layer at an operable distance from said gas flow regulating layer.

27. An apparatus as recited in claim 24, further comprising baffle means for directing a greater amount of said web material fibers toward a center portion of said foraminous web forming layer than toward marginal edge portions thereof.

28. A method for forming a fibrous web, comprising the steps of:
  a. depositing fibers of web material on a foraminous web forming layer by impinging a stream of gas-entrained fibers on said web forming layer while passing the gas component of said stream through said web forming layer;
  b. supporting said web forming layer with spacing means to reduce distortions of the web forming layer while depositing said fibers, said spacing means having rounded support edges which minimize an area of contact with said web forming layer and thereby allow a substantially unrestricted flow of said gas through said spacing means; and
  c. allowing said gas to flow through a gas flow regulating layer, which has a selected pattern of apertures therethrough and is positioned in adjacent facing relation with said supported web forming layer, thereby providing a selected pattern of gas flow through said web forming layer;
  d. said web forming layer, said foraminous spacing means and said gas flow regulating being constructed to form a replaceable web forming assembly.

* * * * *